(12) United States Patent
Richter et al.

(10) Patent No.: US 6,955,687 B2
(45) Date of Patent: Oct. 18, 2005

(54) BIFURCATED STENT WITH IMPROVED SIDE BRANCH APERTURE AND METHOD OF MAKING SAME

(75) Inventors: Jacob Richter, Ramat Hasharon (IL); Gregory Pinchasik, Herzeliya (IL)

(73) Assignee: Medinol Ltd., Tel Aviv (IL)

( * ) Notice: Subject to any disclaimer, the term of this patent is extended or adjusted under 35 U.S.C. 154(b) by 429 days.

(21) Appl. No.: 10/150,652

(22) Filed: May 17, 2002

(65) Prior Publication Data

US 2003/0036793 A1 Feb. 20, 2003

Related U.S. Application Data

(60) Continuation of application No. 09/840,414, filed on Apr. 23, 2001, now Pat. No. 6,436,134, which is a division of application No. 09/072,846, filed on May 5, 1998, now Pat. No. 6,251,133, which is a continuation-in-part of application No. 09/049,842, filed on Mar. 27, 1998, now Pat. No. 6,090,133, which is a continuation of application No. 08/911,606, filed on Aug. 14, 1997, now Pat. No. 5,827,320, which is a continuation of application No. 08/841,702, filed on Apr. 30, 1997, now Pat. No. 5,755,735, which is a division of application No. 08/840,612, filed on Apr. 29, 1997, now Pat. No. 5,755,734, which is a division of application No. 08/642,297, filed on May 3, 1996, now abandoned.

(51) Int. Cl.$^7$ ................................................ A61F 2/06
(52) U.S. Cl. ....................................................... 623/1.35
(58) Field of Search ............................... 623/1.35, 1.11, 623/1.15, 1.16, 1.27; 606/191, 194, 195, 198

(56) References Cited

U.S. PATENT DOCUMENTS

| 4,577,631 A | 3/1986 | Kreamer |
| 4,733,665 A | 3/1988 | Palmaz |
| 4,795,465 A | 1/1989 | Marten |
| 4,896,670 A | 1/1990 | Crittenden |

(Continued)

FOREIGN PATENT DOCUMENTS

| DE | 297 01 758 | 5/1997 |
| EP | 0 551 179 | 7/1993 |
| EP | 0 686 379 | 2/1995 |
| EP | 0804 907 | 11/1997 |
| EP | 0669114 B1 | 6/1998 |
| FR | 2 064 228 | 7/1971 |
| FR | 2 678 508 | 1/1993 |
| SU | 942 736 | 7/1982 |
| SU | 942736 | 7/1982 |
| WO | 95/16406 | 6/1995 |
| WO | WO 95/21592 | 8/1995 |
| WO | 95/21592 | 8/1995 |
| WO | WO 96/34580 | 11/1996 |
| WO | 96/34580 | 11/1996 |
| WO | WO 96/41592 | 12/1996 |
| WO | 96/41592 | 12/1996 |
| WO | 97/46174 | 12/1997 |
| WO | WO 97/46174 | 12/1997 |
| WO | WO 98/19628 | 5/1998 |
| WO | WO 98/36708 | 8/1998 |
| WO | 98/36708 | 8/1998 |

*Primary Examiner*—Kevin T. Truong
(74) *Attorney, Agent, or Firm*—Kenyon & Kenyon

(57) ABSTRACT

A bifurcated stent for insertion into a bifurcated vessel such as a blood vessel. In one embodiment, a first sheet is formed into a first leg, a second sheet is formed into a second leg, a third sheet is formed into a stem, and the two legs are attached to the stem. In a second embodiment, a first sheet is formed into a member having a first leg and half of a stem, a second sheet is formed into a second member having a second leg and half of a stem, and the two stem halves are combined to form the bifurcated stent. In a third embodiment, the stent comprises two sections that are serially inserted and assembled within the vessel at the site of the bifurcation to be treated.

3 Claims, 19 Drawing Sheets

U.S. PATENT DOCUMENTS

| | | | |
|---|---|---|---|
| 4,994,071 A | 2/1991 | MacGregor | |
| 5,219,355 A | 6/1993 | Parodi et al. | |
| 5,316,023 A | 5/1994 | Palmaz et al. | |
| 5,383,892 A | 1/1995 | Cardon et al. | |
| 5,464,449 A | 11/1995 | Ryan et al. | |
| 5,607,444 A | 3/1997 | Lam | |
| 5,609,605 A | 3/1997 | Marshall et al. | |
| 5,609,627 A | 3/1997 | Goicoechea et al. | |
| 5,613,980 A | 3/1997 | Chauhan | |
| 5,617,878 A | 4/1997 | Taheri | |
| 5,632,763 A | 5/1997 | Glastra | |
| 5,669,924 A | 9/1997 | Shaknovich | |
| 5,676,697 A | 10/1997 | McDonald | |
| 5,679,659 A | 10/1997 | Verhoeven et al. | |
| 5,725,572 A | 3/1998 | Lam et al. | |
| 5,749,375 A | 5/1998 | Maginot | |
| 5,755,734 A | 5/1998 | Richter | |
| 5,755,735 A | 5/1998 | Richter et al. | |
| 5,755,771 A | 5/1998 | Penn et al. | |
| 5,766,238 A | 6/1998 | Lau et al. | |
| 5,782,906 A | 7/1998 | Marshall et al. | |
| 5,824,042 A | 10/1998 | Lombardi et al. | |
| 5,824,043 A | 10/1998 | Cottone, Jr. | |
| 5,824,052 A | 10/1998 | Khosravi et al. | |
| 5,824,056 A | 10/1998 | Rosenberg | |
| 5,827,320 A | 10/1998 | Richter et al. | |
| 5,833,707 A | 11/1998 | McIntyre et al. | |
| 5,843,160 A | 12/1998 | Rhodes | |
| 5,855,598 A | 1/1999 | Pinchuk | |
| 5,861,027 A | 1/1999 | Trapp | |
| 5,906,640 A | 5/1999 | Penn et al. | |
| 5,906,641 A | 5/1999 | Thompson et al. | |
| 5,916,263 A | 6/1999 | Goicoechea et al. | |
| 5,961,548 A | 10/1999 | Shmulewitz | |
| 5,972,017 A | 10/1999 | Berg et al. | |
| 5,984,955 A | 11/1999 | Wisselink | |
| 6,017,363 A | 1/2000 | Hojeibane | |
| 6,033,434 A | 3/2000 | Borghi | |
| 6,033,435 A * | 3/2000 | Penn et al. | 623/1.15 |
| 6,096,073 A | 8/2000 | Webster et al. | |
| 6,117,156 A | 9/2000 | Richter et al. | |
| 6,162,243 A | 12/2000 | Gray et al. | |
| 6,165,195 A | 12/2000 | Wilson et al. | |
| 6,190,353 B1 | 2/2001 | Makower et al. | |
| 6,203,568 B1 * | 3/2001 | Lombardi et al. | 623/1.35 |
| 6,210,429 B1 | 4/2001 | Vardi et al. | |
| 6,346,089 B1 * | 2/2002 | Dibie | 623/1.11 |
| 6,406,489 B1 | 6/2002 | Richter et al. | |

* cited by examiner

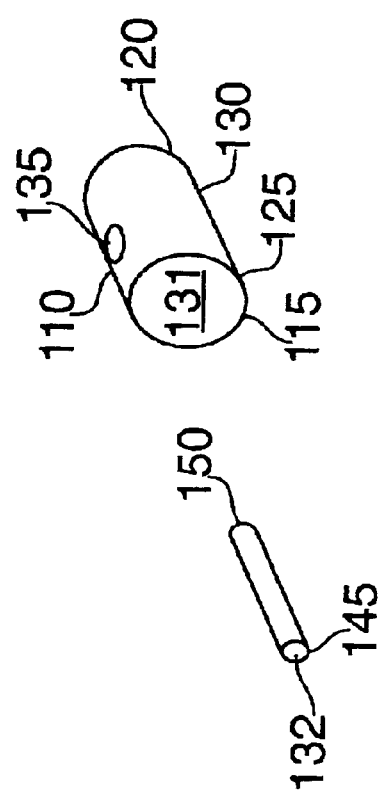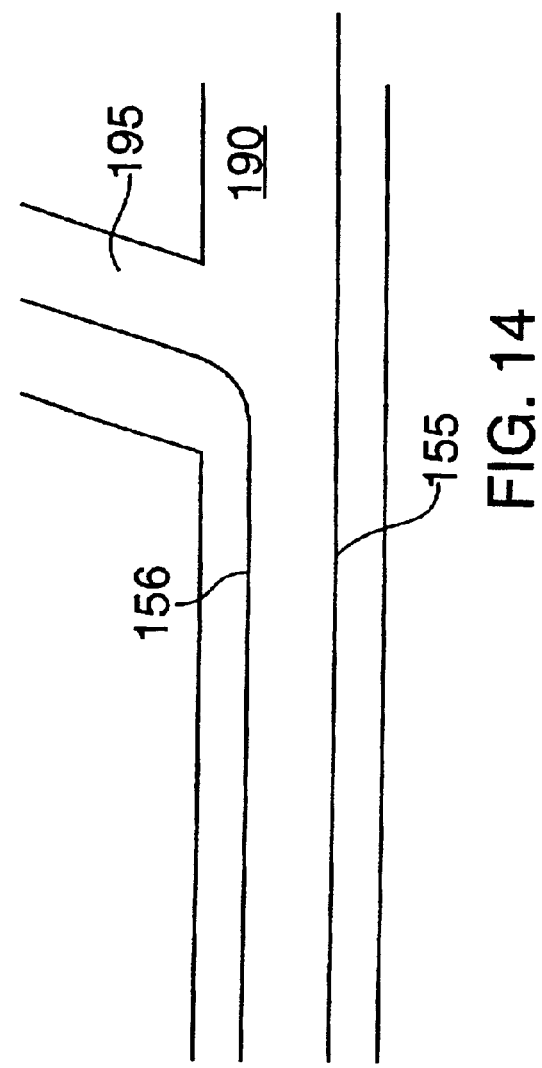

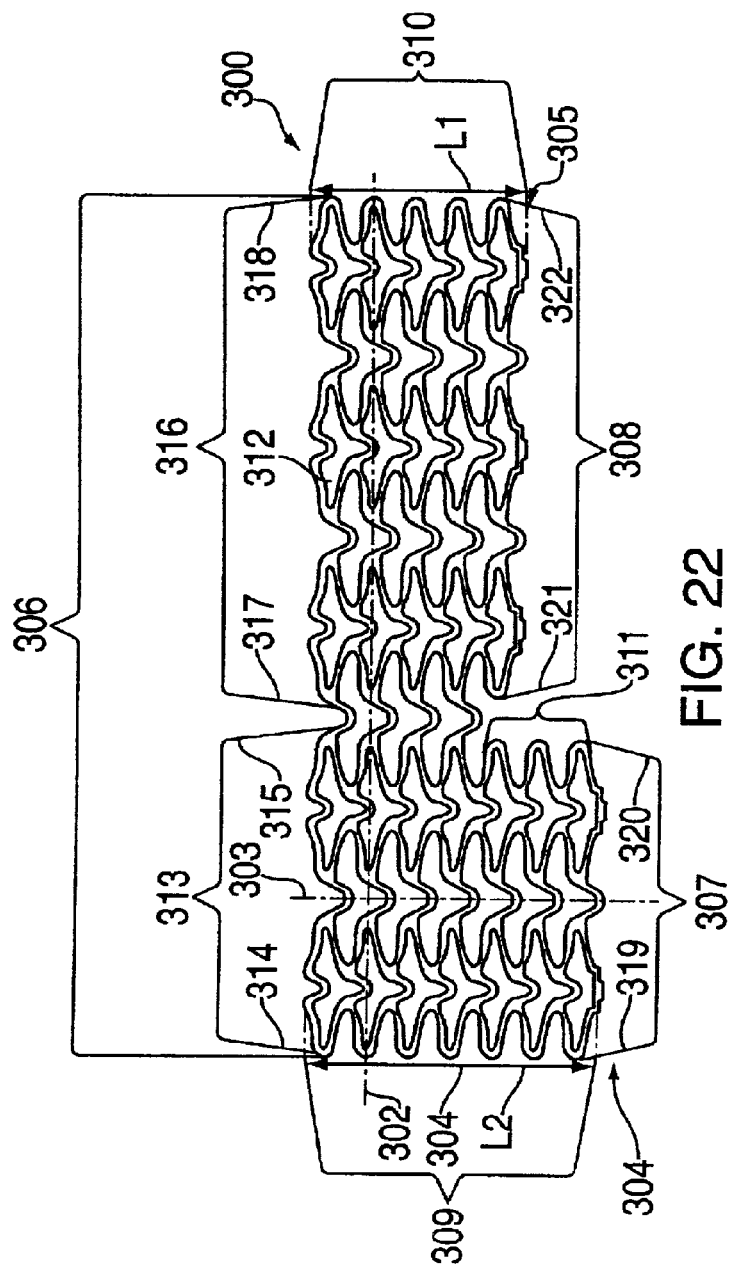
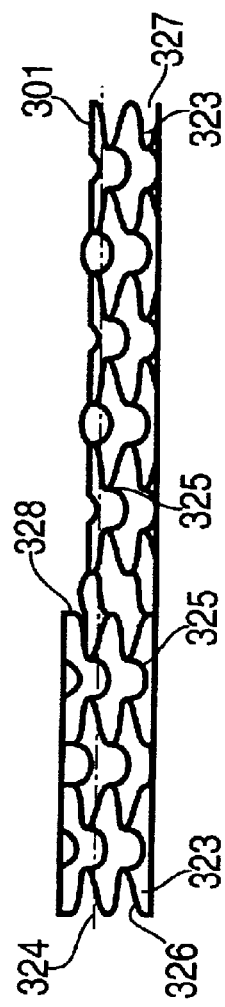
FIG. 22
FIG. 23

BIFURCATED STENT WITH IMPROVED SIDE BRANCH APERTURE AND METHOD OF MAKING SAME

This application is a continuation of U.S. patent application Ser. No. 09/840,414 filed on Apr. 23, 2001 now U.S. Pat. No. 6,436,134 which is a division of U.S. patent application Ser. No. 09/072,846 filed May 5, 1998 now U.S. Pat. No. 6,251,133, which is a continuation-in-part of Ser. No. 09/049,842 filed Mar. 27, 1998 now U.S. Pat. No. 6,090,133, which is a continuation of 08/911,606 filed Aug. 14, 1997 now U.S. Pat. No. 5,827,320, which is a continuation of Ser. No. 08/841,702 filed Apr. 30, 1997, now U.S. Pat. No. 5,755,735, which is a division of Ser. No. 08/840,612 filed Apr. 29, 1997 now U.S. Pat. No. 5,755,734; which is a division of Ser. No. 08/642,297 filed May 3, 1996 (now abandoned).

FIELD OF THE INVENTION

The present invention relates to stents, and more particularly to bifurcated stents and methods of making bifurcated stents for insertion within a branching vessel.

BACKGROUND OF THE INVENTION

Stents are well known in the art. They are typically formed of a cylindrical metal mesh which can expand when pressure is internally applied. Alternatively, they can be formed of wire wrapped into a cylindrical shape or sheets of material formed into a cylindrical shape.

Stents are devices which are usually implanted within bodily conduits including the vascular system to reinforce collapsing, partially occluded, weakened, or abnormally dilated sections of the blood vessel. Stents also have been successfully implanted in other areas, e.g., the urinary tract or the bile duct to reinforce such bodily conduits.

U.S. Pat. No. 4,994,071 (MacGregor) discloses an expandable, bifurcating stent having a main cylindrical lattice formed from interconnected, flexible wire. Two additional cylindrical lattices, having smaller diameters than the main lattice, are similarly constructed. The main lattice includes a flexible wire interconnecting the main lattice to one of the additional lattices. A second flexible wire interconnects the main lattice to the other additional lattice. The flexible wires form backbones that extend axially along the length of the main lattice and along each of the additional lattices. One disadvantage of this bifurcating stent is the complex nature of the interconnection of the flexible wires forming the backbones with the loop structure of each lattice.

SUMMARY OF THE INVENTION

The present invention solves these and other disadvantages of the prior art by providing bifurcated stents and methods of fabricating and deploying bifurcated stents having a stem portion and two leg portions.

In a first embodiment of the invention, a bifurcated stent is made by providing three sheets patterned to a desired pattern, wherein two sheets are substantially the same size and the third sheet is wider than either of the first two sheets. Each of the sheets is formed into tubes by turning up the longitudinal edges and forming a joint by welding. The larger sheet forms a tube that acts as the stem portion of the bifurcated stent and the other sheets form tubes which act as the leg portions of the bifurcated stent. The two leg portions are then joined to the stem portion to form the bifurcated stent.

In a second embodiment of the invention, the bifurcated stent is formed by preparing two stent sheets. For each sheet, the longitudinal edges of a portion of the sheet are turned up and secured to each other to form one of the two leg portions of the bifurcated stent. The remaining free edges of each of the two sheets are then joined to form the stem portion of the stent.

In a third embodiment, the bifurcated stent comprises first and second tubular portions. The first portion has a proximal end which forms the stem portion and a distal end which forms one of the leg portions of the bifurcated stent. A branch aperture is disposed between the proximal end and the distal end of the first portion. The second portion is introduced into the longitudinal bore of the stem portion of the first portion and is advanced through the branch aperture so that it protrudes beyond the branch aperture to form a second leg. When the second portion is expanded, the proximal end of the second portion engages the material defining the branch aperture so as to secure the second leg in the desired position.

It is an object of this invention to provide a method of making a bifurcated stent, comprising the steps of: a) preparing a first sheet having a first edge, a second edge, a third edge, and a fourth edge; b) preparing a second sheet having a first edge, a second edge, a third edge, and a fourth edge; c) preparing a third sheet having a first edge, a second edge, a third edge, and a fourth edge; d) attaching the second edge to the third edge of the first sheet to form a tubular first leg portion having a proximal end and a distal end; e) attaching the second edge to the third edge of the second sheet to form a tubular second leg portion having a proximal end and a distal end; f) attaching the second edge to the third edge of the third sheet to form a tubular stem portion having a proximal end and a distal end; and g) attaching the proximal end of the first leg portion and the proximal end of the second leg portion to the distal end of the stem portion.

It is another object of this invention to provide a method of making a bifurcated stent, comprising the steps of a) preparing a first sheet having a proximal end and a distal end; b) deforming the distal end of the first sheet to form a first leg and deforming the proximal end of the first sheet to form a first stem half; c) preparing a second sheet having a proximal end and a distal end; d) deforming the distal end of the second sheet to form a second leg and deforming the proximal end of the second sheet to form a second stem half; and e) joining the first stem half to the second stem half to form a stem.

It is yet another object of this invention to provide a method of making a bifurcated stent comprising the steps of a) preparing a first expandable tubular member having a proximal end and a distal end and a longitudinal bore therethrough, the first tubular member provided with a branch aperture disposed between said proximal end and the distal end, the branch aperture communicating with said longitudinal bore and the aperture sized and adapted to receive and secure a second expandable tubular member; b) delivering the first expandable tubular member to a bifurcated vessel having a first lumen and a second lumen so that the first expandable member is disposed within the first lumen and the branch aperture communicates with the second lumen; c) expanding the first expandable member in an amount sufficient to secure the first expandable member in the first lumen; d) preparing a second expandable tubular member having a proximal end and a distal end and having longitudinal bore therethrough; e) widening the branch aperture; f) delivering the second expandable tubular member into the branch aperture so that the distal end of the second expandable tubular member is disposed within the second lumen and the proximal end of the second expandable tubular member is disposed within the longitudinal bore of the first longitudinal member; and g) expanding the second expandable tubular member in an amount sufficient to secure the second expandable tubular member within the second lumen and within said branch aperture.

BRIEF DESCRIPTION OF THE DRAWINGS

FIG. 13 shows a stem and first leg portion and a second leg portion used to form another embodiment of a bifurcated stent manufactured in accordance with this invention;

FIG. 14 shows guide wires disposed in the trunk lumen and branch lumen to be treated;

FIG. 22 shows a sheet used to form a first expandable tubular member;

FIG. 23 shows the sheet of FIG. 22 after it has been formed into a first expandable tubular member;

DETAILED DESCRIPTION

Figure 1:
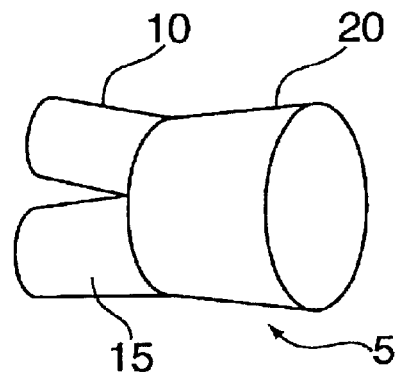
FIG. 1 shows a bifurcated stent manufactured in accordance with the present invention.
Figure 2:
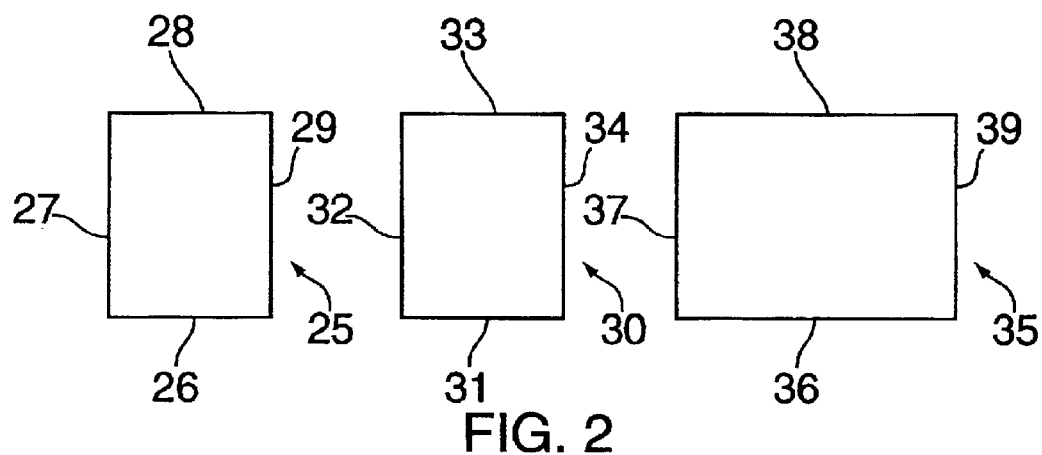
FIG. 2 shows sheets used to form the legs and stem of the stent shown in FIG. 1.

In the embodiment illustrated in FIG. 1, the bifurcation stent 5 comprises a first leg 10, a second leg 15, and a stem 20. FIG. 2 shows a first sheet 25 which is used to form first leg 10, a second sheet 30 which is used to form second leg 15, and a third sheet 35 which is used to form stem 20. The first sheet 25 and second sheet 30 are substantially flat and are sized to a predetermined length and width. For many applications, the first sheet 25 and second sheet 30 will have substantially the same dimensions so as to produce legs 10 and 15 that are substantially the same size, however, the legs 10 and 15, and the sheets 25 and 30 used to produce them, may be of varying sizes as specific applications dictate. The stents of this invention may be sized so that when assembled they are their final size, however, in a preferred embodiment the stents are expandable and sized and adapted to assume their final dimensions upon expansion. The stent sheets 70 and 75 may be patterned or etched with perforations forming a variety of patterns as specific applications dictate to achieve the expandable features required as previously discussed. The third sheet 35 is sized so that when it is rolled into a tube its internal cross-section can be made to accommodate the cross-sectional external diameters of first leg 10 and second leg 15. First sheet 25 has a first edge 26, a second edge 27, a third edge 28, and a fourth edge 29. Second sheet 30 has a first edge 31, a second edge 32, a third edge 33, and a fourth edge 34. Third sheet 35 has a first edge 36, a second edge 37, a third edge 38, and a fourth edge 39. After the sheet metal has been cut to form sheets 25, 30, and 35, it is deformed and rolled so as to cause two opposite edges to meet and create a cylinder. In the example shown in FIGS.

Figure 3:
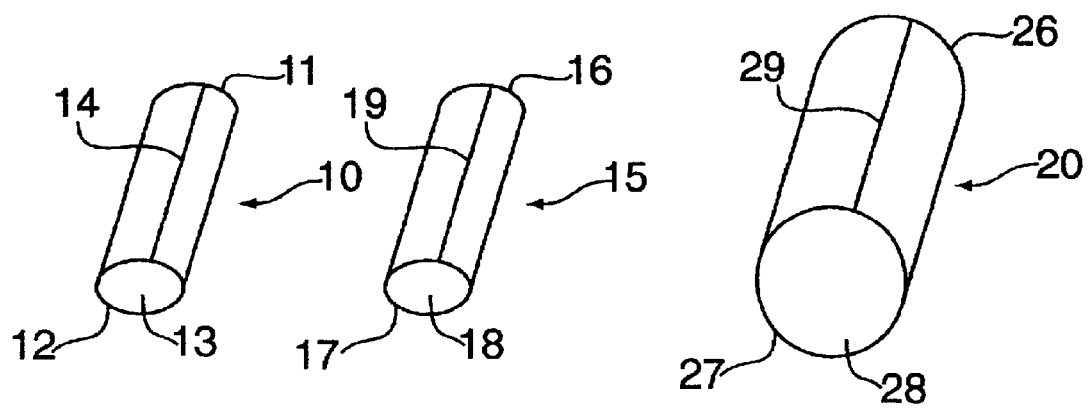
FIG. 3 shows the sheets shown in FIG. 2 after they have been rolled into a tubular shape.
Figure 4:
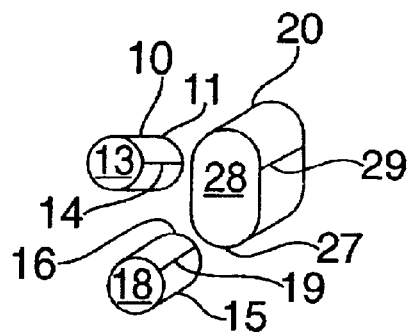
FIG. 4 is a perspective view of the tubes shown in FIG. 3 prior to assembly.
Figure 5:
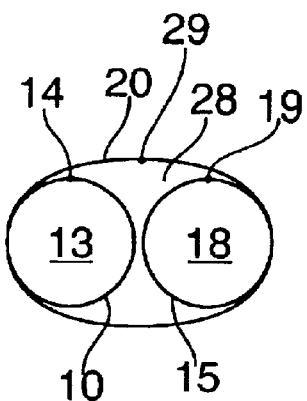
FIG. 5 is an end view of the tubes shown in FIGS. 3 and 4 after they have been assembled to form a stent.
Figure 6:
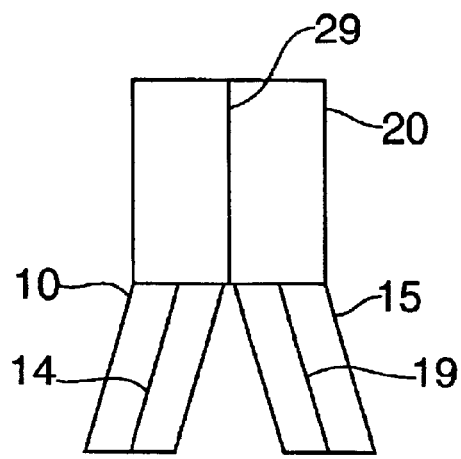
FIG. 6 is a top view of the assembled apparatus shown in FIG. 5.

2 and 3, edge 27 is joined to edge 29 via weld run 14 to form first leg 10. Edge 32 is joined to edge 34 via weld run 19 to form second leg 15. Edge 37 is joined to edge 39 via weld run 29 to form stem 20. The edges may be joined in a wide variety of ways well known to those skilled in the art as suitable for this purpose, e.g., screwing, crimping, soldering, however, in a preferred embodiment welding is utilized. In an especially preferred embodiment, spot welding is utilized. As shown in FIG. 3, first leg 10 has a proximal end 11, a distal end 12, and defines a longitudinal bore 13. Second leg 15 has a proximal end 16, a distal end 17, and defines a longitudinal bore 18. The stem 20 has a proximal end 26, a distal end 27, and defines a longitudinal bore 28. FIG. 4 shows the first leg 10, second leg 15, and stem 20 just prior to assembly. To form the bifurcated stent 5, the proximal end 11 of first leg 10 and the proximal end 16 of second leg 15 are joined to the distal end 27 of the stem portion 20 so that the longitudinal bores 13, 18, and 28 are in communication with each other. FIG. 5 is an end view and FIG. 6 is a side view of the assembled apparatus.

Figure 7:
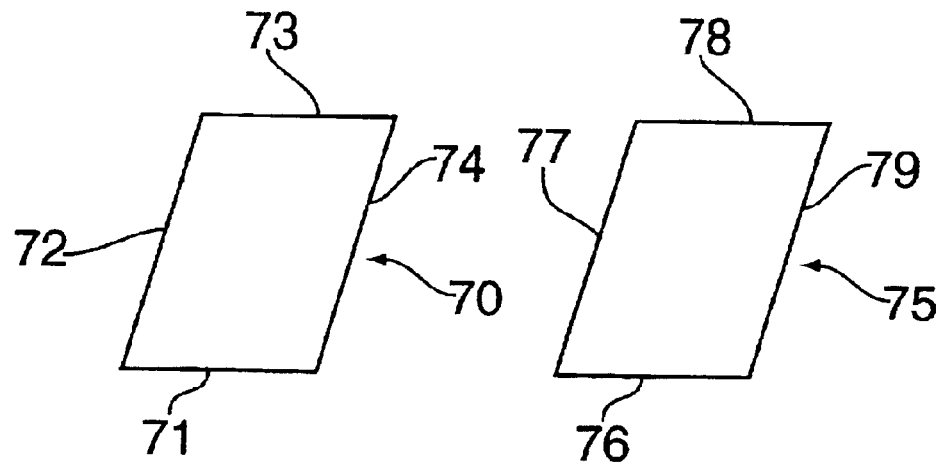
FIG. 7 shows sheets used to form another embodiment of a bifurcated stent manufactured in accordance with the invention.
Figure 8:
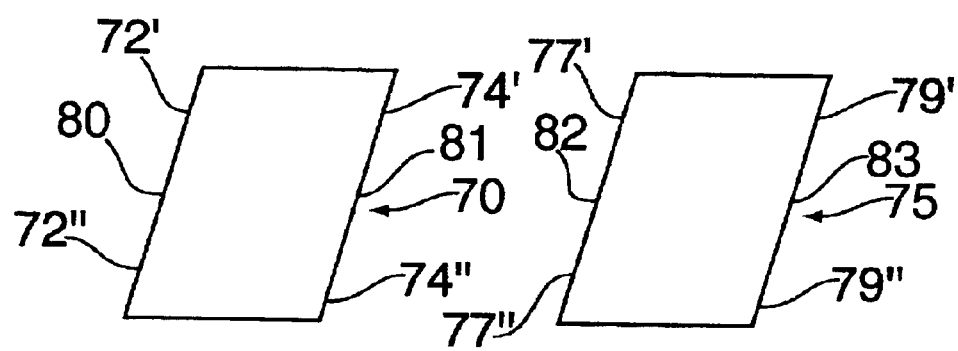
FIG. 8 shows the sheets of FIG. 7 with demarcation points.
Figure 11:
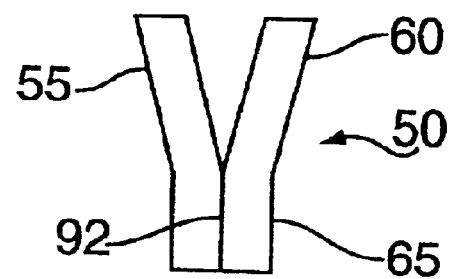
FIG. 11 is a side view of the tubes shown in FIGS. 9 and 10 after assembly.

FIG. 11 shows a second embodiment of a bifurcation stent manufactured in accordance with this invention. The stent 50 is provided with a first leg 55 and a second leg 60 attached to a stem portion 65. The bifurcation stent 50 is formed from a first sheet 70 and a second sheet 75 as shown in FIG. 7. The stent sheets 70 and 75 may be patterned or etched with perforations forming a variety of patterns as specific applications dictate to achieve the expandable features required as previously discussed. The sheets 70 and 75 are substantially flat and have a predetermined length and width. First sheet 70 has a first edge 71, a second edge 72, a third edge 73 and a fourth edge 74. The second sheet 75 has a first edge 76, a second edge 77, a third edge 78, and a fourth edge 79. To form the legs of the stent a portion of edge 72 is rolled towards a portion of edge 74 and a portion of edge 77 is rolled towards a portion of edge 79. Demarcation points 80, 81, 82, and 83 are selected on sheets 70 and 75 as shown in FIG. 8. These demarcation points 80, 81, 82, and 83 are selected to meet the requirement of specific applications and may be adjusted depending upon the length required for legs 55 and 60 and the length required for stem 65. Demarcation points 80 and 81 that are equidistant from edges 73 and 71 and demarcation points 82 and 83 that are equidistant from edges 76 and 78 will result in a stent in which the legs 55 and 60 have a length that is substantially equal to stem portion 65. If the demarcation points are selected to be closer to edges 73 and 78 than to edges 71 and 76 the stem will have a length that is greater than the length of each of the legs. If the demarcation points are selected to be closer to edges 71 and 76 than to edges 73 and 78, each of the legs 60 and 65 will have a length that is greater than the length of the stem 65. In a preferred embodiment, however, the demarcation points 80, 81, 82, and 83, are selected so that proximal edges 72", 74", 77", and 79" are about ⅓ the length of edges 72, 74, 77, and 79. As shown in FIG. 8, demarcation point 80 divides edge 72 at approximately its midpoint into a distal edge 72' and a proximal edge 72". Demarcation point 81 divides edge 74 at approximately its midpoint into a distal edge 74' and a proximal edge 74". Demarcation point 82 divides edge 77 at approximately its midpoint into a distal edge 77' and a proximal edge 77" and demarcation point 83 divides edge 79 at approximately its midpoint into a distal edge 79' and a proximal edge 79".

Figure 9:
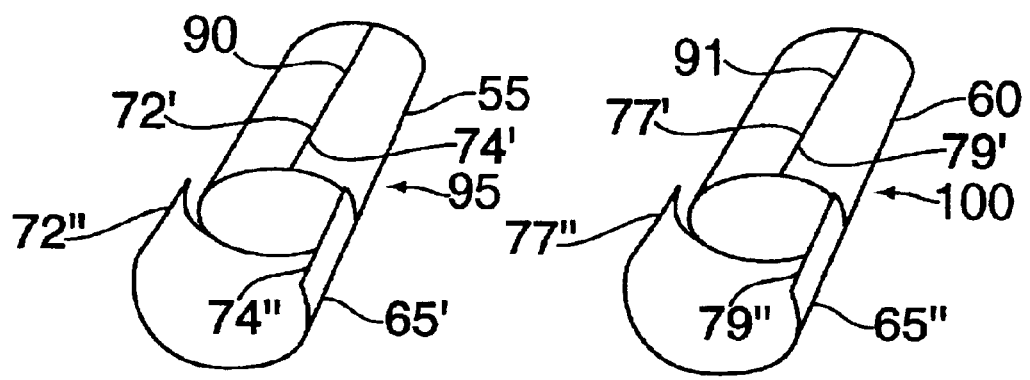
FIG. 9 shows the sheets of FIG. 8 after they have been rolled into a tubular shape.
Figure 10B:
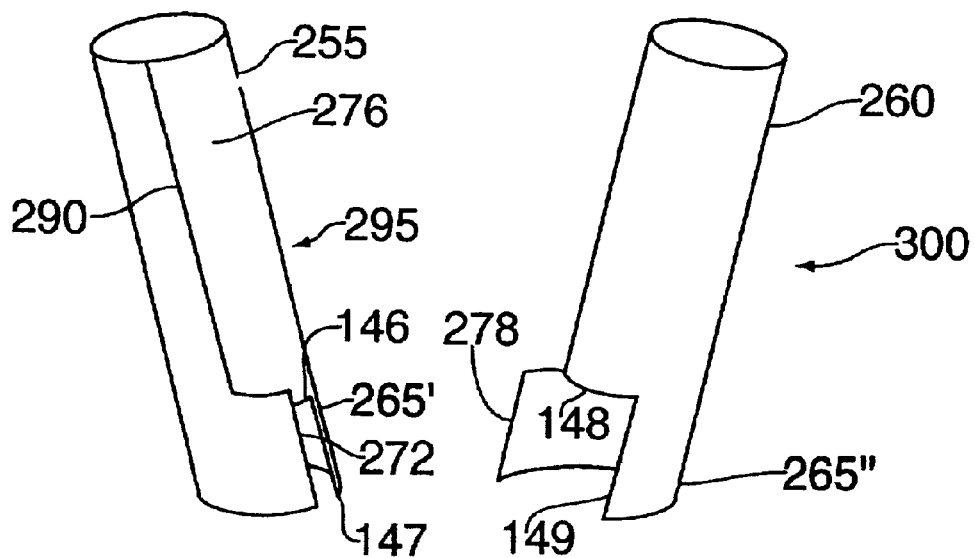
FIG. 10B shows the tubes of FIG. 9B just prior to assembly.
Figure 10:
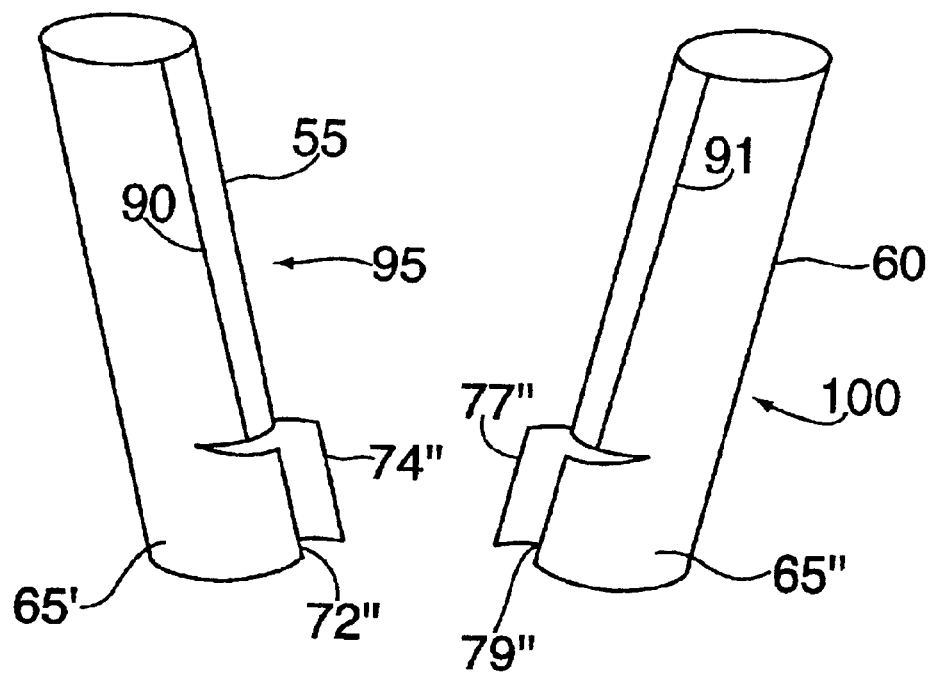
FIG. 10 shows the tubes of FIG. 9 just prior to assembly.
Figure 12B:
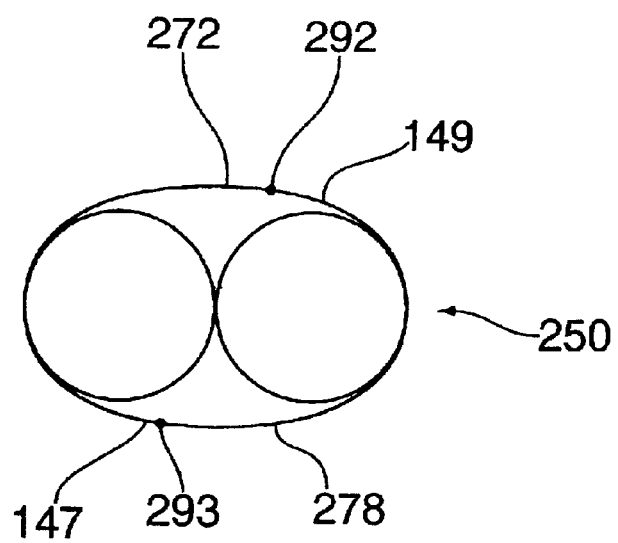
FIG. 12B is an end view of the assembled apparatus shown in FIG. 11B.
Figure 12C:
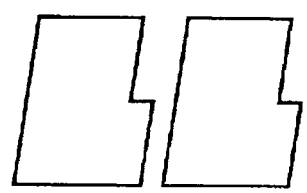
FIG. 12C shows an alternative embodiment of a pattern that may be used in place of the patterns shown in FIGS. 7 and 7B.
Figure 12:
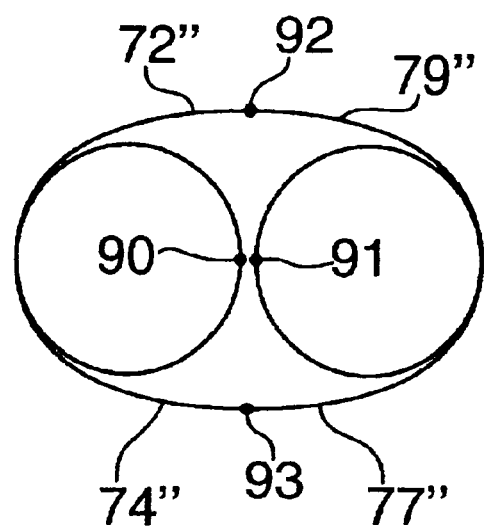
FIG. 12 is an end view of the assembled apparatus shown in FIG. 11.

To form the stent, edge 72' is connected to edge 74' via weld run 90 to form first member 95 having a first leg portion 55 and a first stem half 65' as shown in FIG. 9. Edge 77' is connected to edge 79' via weld run 91 to form second member 100 having a second leg portion 60 and a second stem half 65". As previously discussed, the edges may be connected in a variety of ways well known to those skilled in the art. FIG. 10 shows the first member 95 and the second member 100 shown in FIG. 9 in alignment just prior to assembly. To produce the bifurcated stent 50 shown in FIGS. 11 and 12, edge 72" is connected to edge 79" via weld run 92 and edge 74" is connected to edge 77" via weld run 93 so that first stem half 65' and second stem half 65" form stem 65. FIG. 12 is a cross-sectional end view of the stent shown in FIG. 11.

Figure 7B:
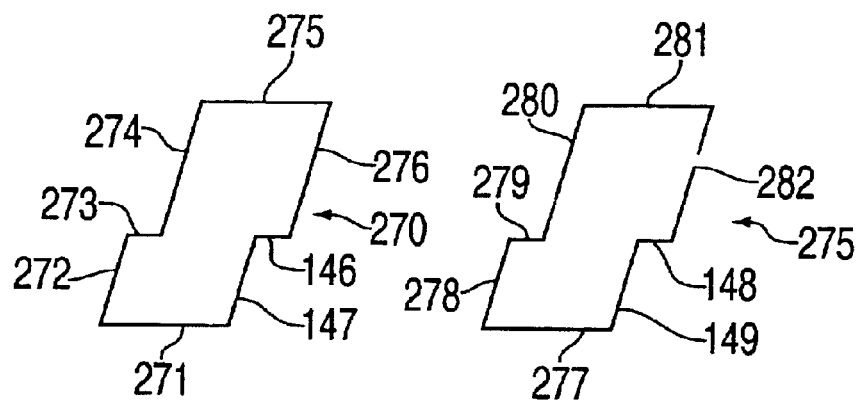
FIG. 7B shows sheets used to form another embodiment of a bifurcated stent manufactured in accordance with the invention.
Figure 9B:
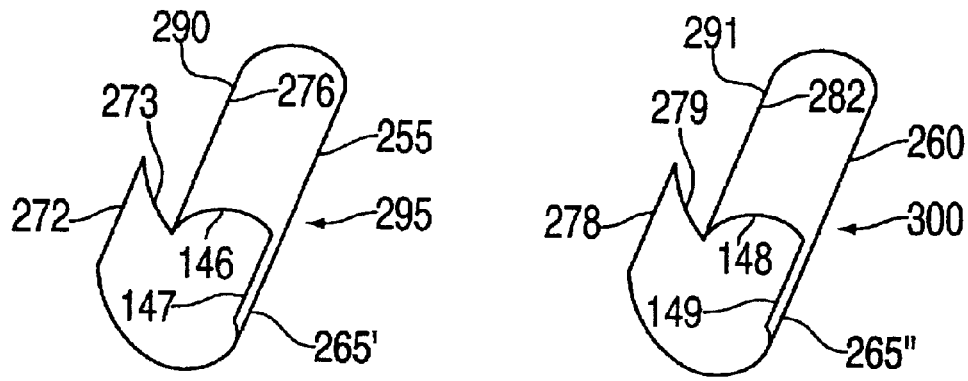
FIG. 9B shows the sheets of FIG. 7B after they have been rolled into a tubular shape.
Figure 11B:
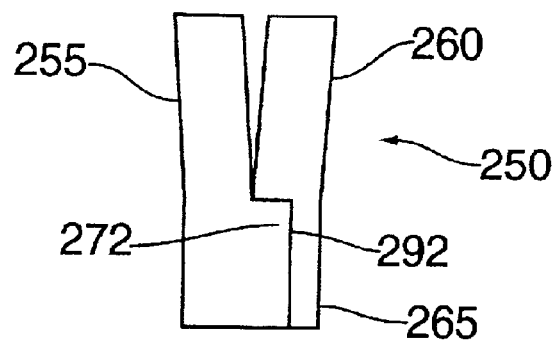
FIG. 11B is a side view of the tubes shown in FIGS. 9B and 10B after assembly.

In the embodiment shown in FIG. 7, sheets 70 and 75 are squares or rectangles. The sheets 70 and 75 are not limited to this configuration, however, as shown in FIG. 7B. FIG. 11B shows a bifurcation stent manufactured using the sheets 270 and 275 shown in FIG. 7B. The stent 250 is provided with a first leg 255 and a second leg 260 attached to a stem portion 265. The bifurcation stent 250 is formed from a first sheet 270 and a second sheet 275 as shown in FIG. 7B. The stent sheets 270 and 275 may be sized and etched as previously discussed. As shown in FIG. 7B, first sheet 270 has a first edge 271, a second edge 272, a third edge 273, a fourth edge 274, a fifth edge 275, and a sixth edge 276, a seventh edge 146, and an eighth edge 147. The second sheet 275 has a first edge 277, a second edge 278, a third edge 279, a fourth edge 280, a fifth edge 281, a sixth edge 282, a seventh edge 148, and an eighth edge 149. As shown in FIG. 9B, edge 274 is connected to edge 276 via weld run 290 to form first member 295 having a first leg portion 255 and a first stem half 265'. Edge 280 is connected to edge 282 via weld run 291 to form second member 300 having a second leg portion 260 and a second stem half 265". As previously discussed, the edges may be connected in a variety of ways well known to those skilled in the art. FIG. 10B shows the first member 295 and the second member 300 shown in FIG. 9B in alignment just prior to assembly. To produce the bifurcated stent 250 shown in FIGS. 11B and 12B, edge 272 is connected to edge 149 via weld run 292 and edge 278 is connected to edge 147 via weld run 293 so that first stem half 265' and second stem half 265" form stem 265. FIG. 12B is a cross-sectional end view of the stent shown in FIG. 11B. FIG. 12C shows an alternative pattern that may be used in place of the patterns shown in FIGS. 7 and 7B.

Figure 15:
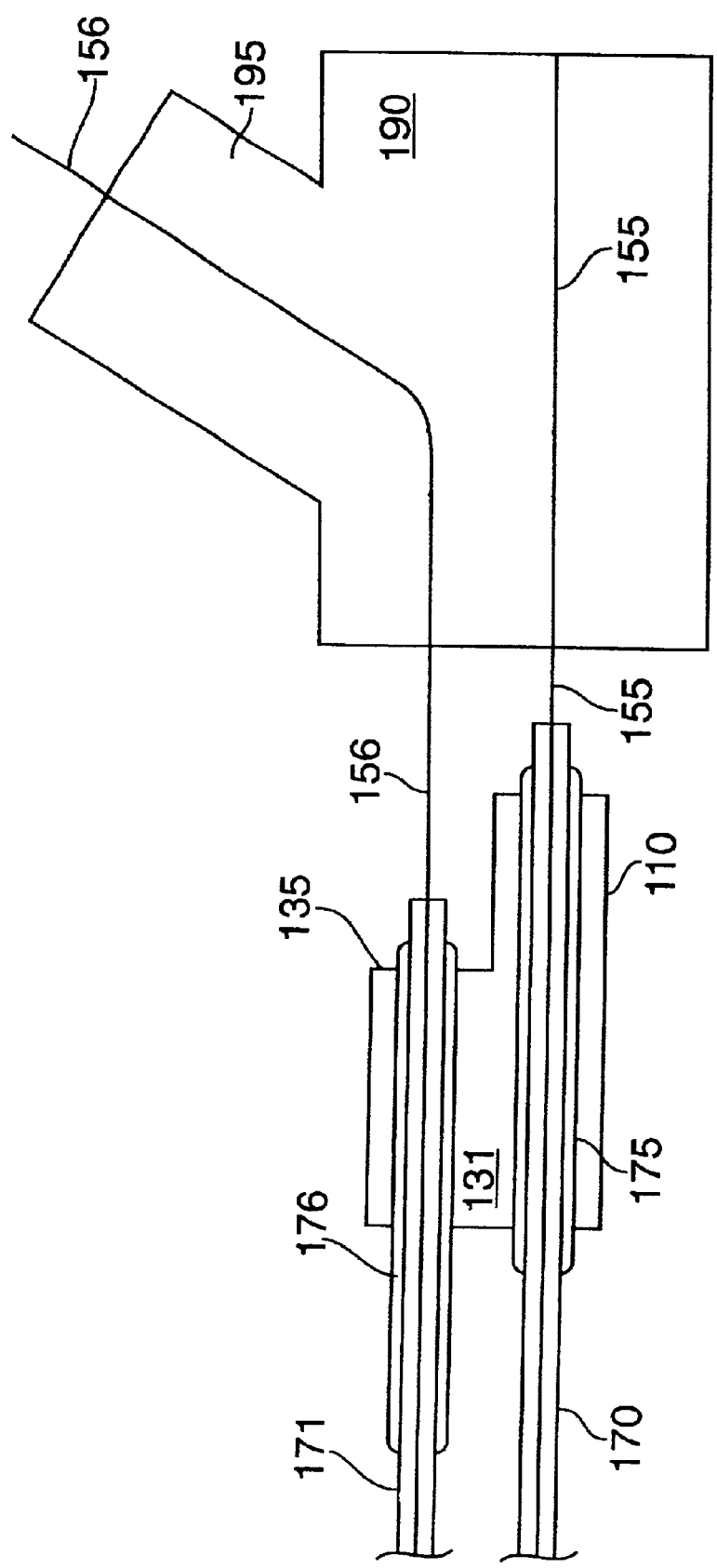
FIG. 15 shows the stem and first leg portion shown in FIG. 13 disposed on catheters and guide wires prior to introduction into the lumen to be treated.
Figure 16:
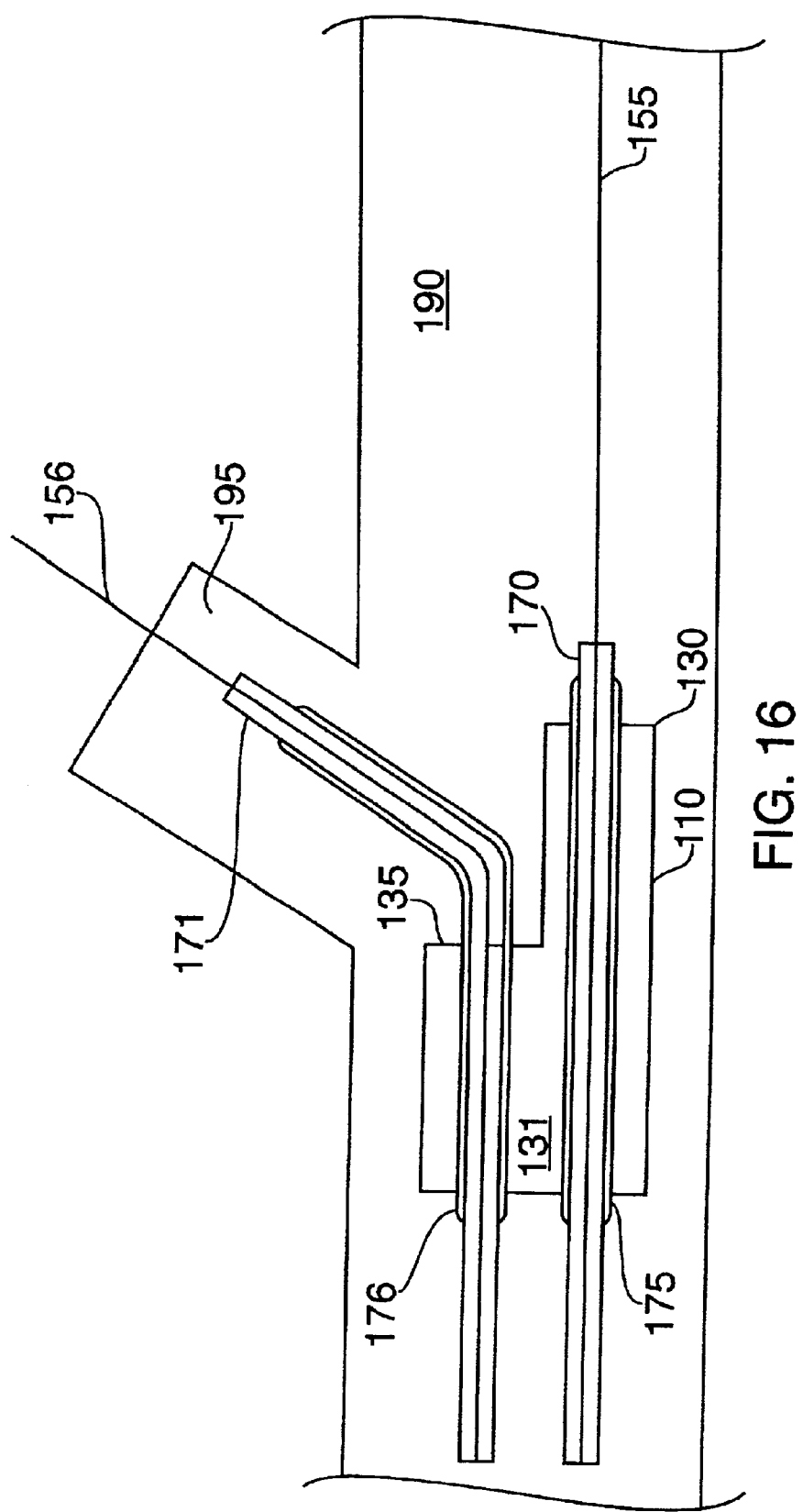
FIG. 16 shows the stem and first leg portion shown in FIG. 13 after it has been delivered to the bifurcation to be treated and prior to its expansion.
Figure 17:
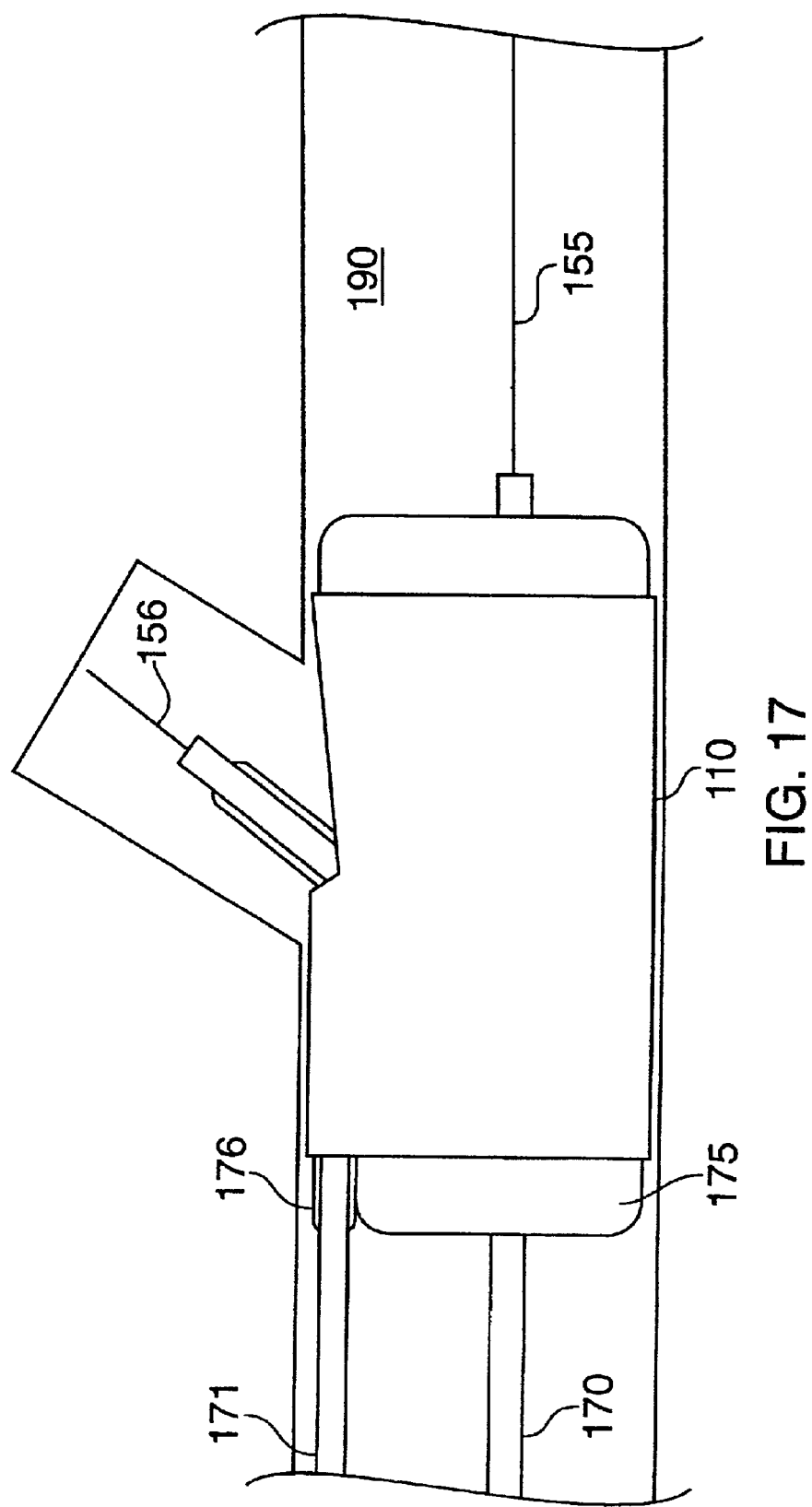
FIG. 17 shows the second leg portion shown in FIG. 16 after it has been expanded.
Figure 18:
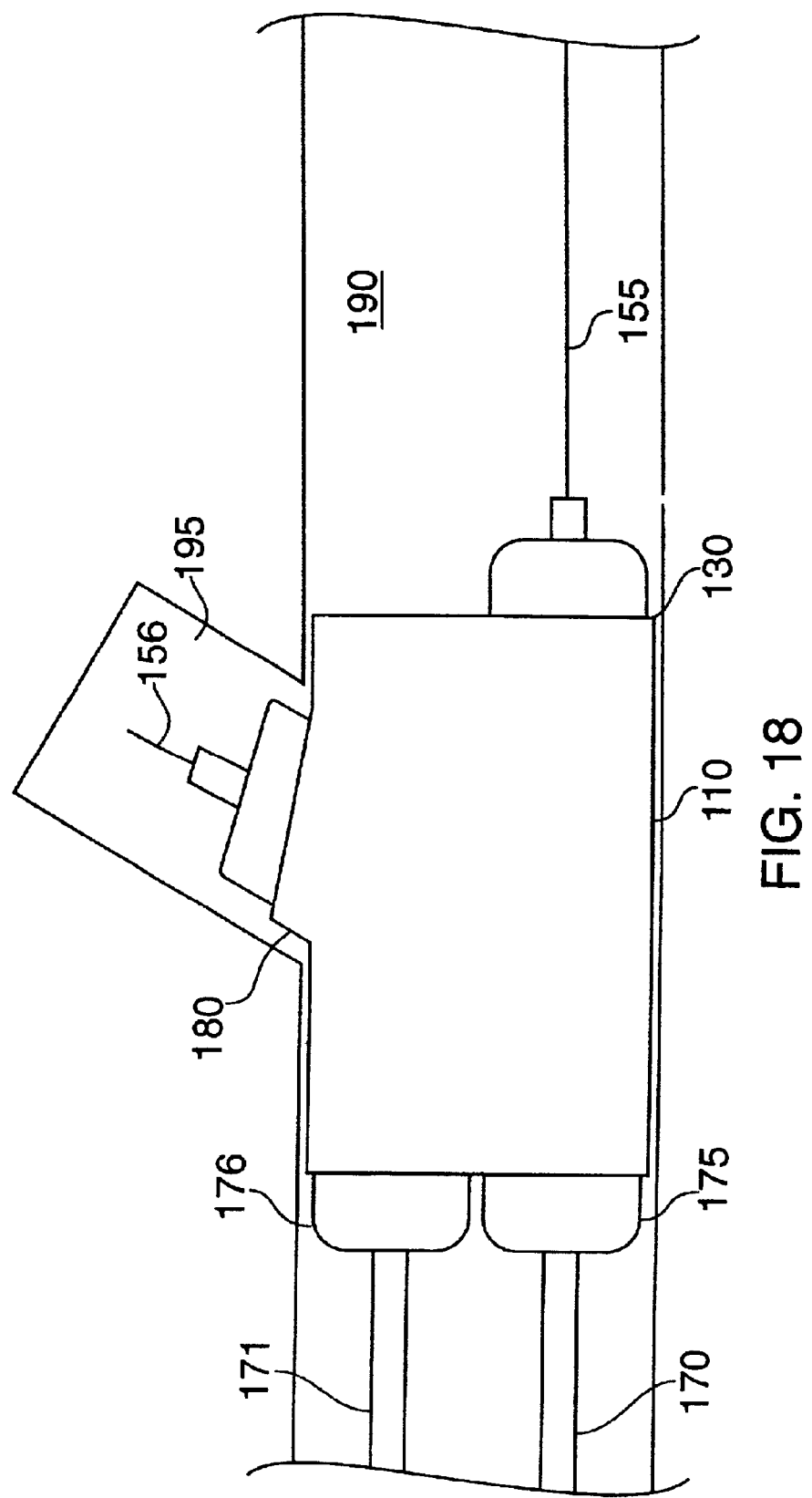
FIG. 18 shows expansion of the branch aperture.

A third embodiment of this invention comprises two portions which are deployed serially in two steps and assembled within the patient to form a bifurcated stent. FIG. 13 shows stem and first leg portion 110 provided with a longitudinal bore 131 and having a proximal end 115 defining a stem portion 125 and a distal end 120 defining a first leg portion 130. Second leg portion 140 is provided with a longitudinal bore 132 and has a proximal end 145 and a distal end 150. Stem and first leg portion 110 and second leg portion 140 may be sized and patterned or etched as previously discussed. A branch aperture 135 is disposed between the proximal end 115 and the distal end 120 of stem and first leg portion 110. The branch aperture 135 is sized to receive second leg portion 140 and is adapted to engage and secure the second leg portion 140 when it has been expanded within the branch aperture 135. Second leg portion 140 is sized and adapted to engage and be secured into branch aperture 135 upon expansion. FIGS. 14 to 21 show how the bifurcated stent is assembled within a bifurcated lumen. As shown in FIGS. 14 to 21, the area to be treated is a bifurcated lumen having a first or trunk lumen 190 and a second or branch lumen 195. As shown in FIG. 14, a first guide wire 155 is introduced into the trunk lumen 190 and a second guide wire 156 is introduced into the branch lumen 195. As shown in FIG. 15, a balloon expandable stem and first leg portion 110 is disposed on the tip of a first balloon catheter 170 so that the balloon 175 is disposed within longitudinal bore 131. A second balloon catheter 171 is then introduced into longitudinal bore 131 of stem and first leg portion 110 and is advanced so that the balloon 176 is disposed within aperture 135. First catheter 170 is mounted on first guide wire 155 and second catheter 171 is mounted on second guide wire 156. As shown in FIG. 16, the unexpanded stem and first leg portion 110 is guided to the area to be treated so that first leg portion 130 is disposed within trunk lumen 190 and branch aperture 135 communicates with branch lumen 195. Guide wire 156 facilitates the orientation of the branch aperture 135 with the branch lumen 195. The size of the conventional catheters and balloons is not to scale and details well known to those skilled in the art have been omitted for clarity. Balloon 175 is inflated which causes the stem and first leg portion 110 to expand, as shown in FIG. 17, to secure it in the desired position. After expansion, the external wall of stem and first leg portion 110 would contact the interior walls of trunk lumen 190, however, a gap has been intentionally left for clarity. The balloon 175 on first catheter 170 is left inflated and the balloon 176 on second catheter 171 is then inflated to enlarge the branch aperture 135 as shown in FIG. 18. As the branch aperture 135 is enlarged a portion of the stent defining the branch aperture 135 is pushed outward to form a branch securing lip 180.

Figure 19:
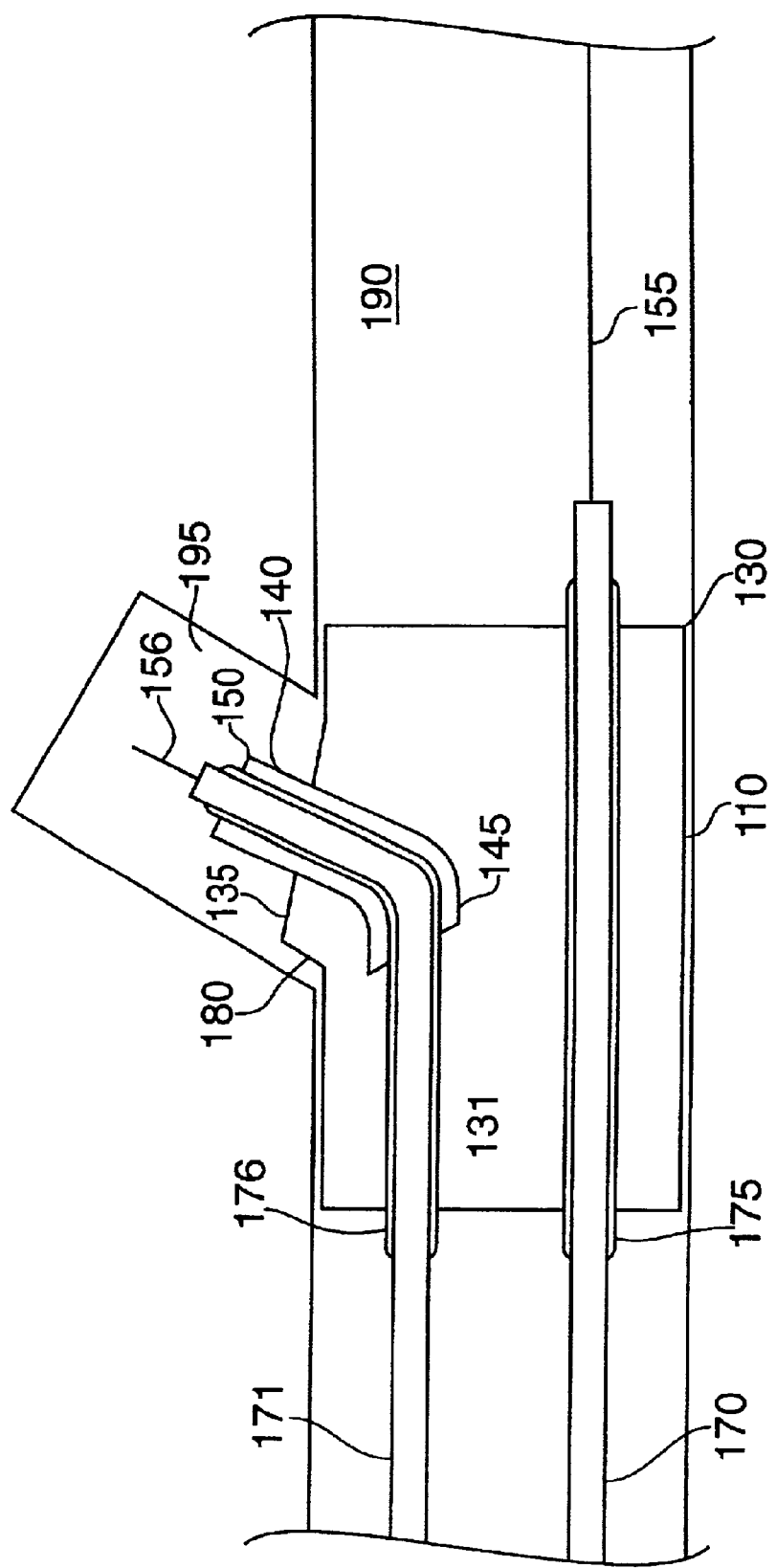
FIG. 19 shows the unexpanded second leg portion disposed in the branch aperture.
Figure 20:
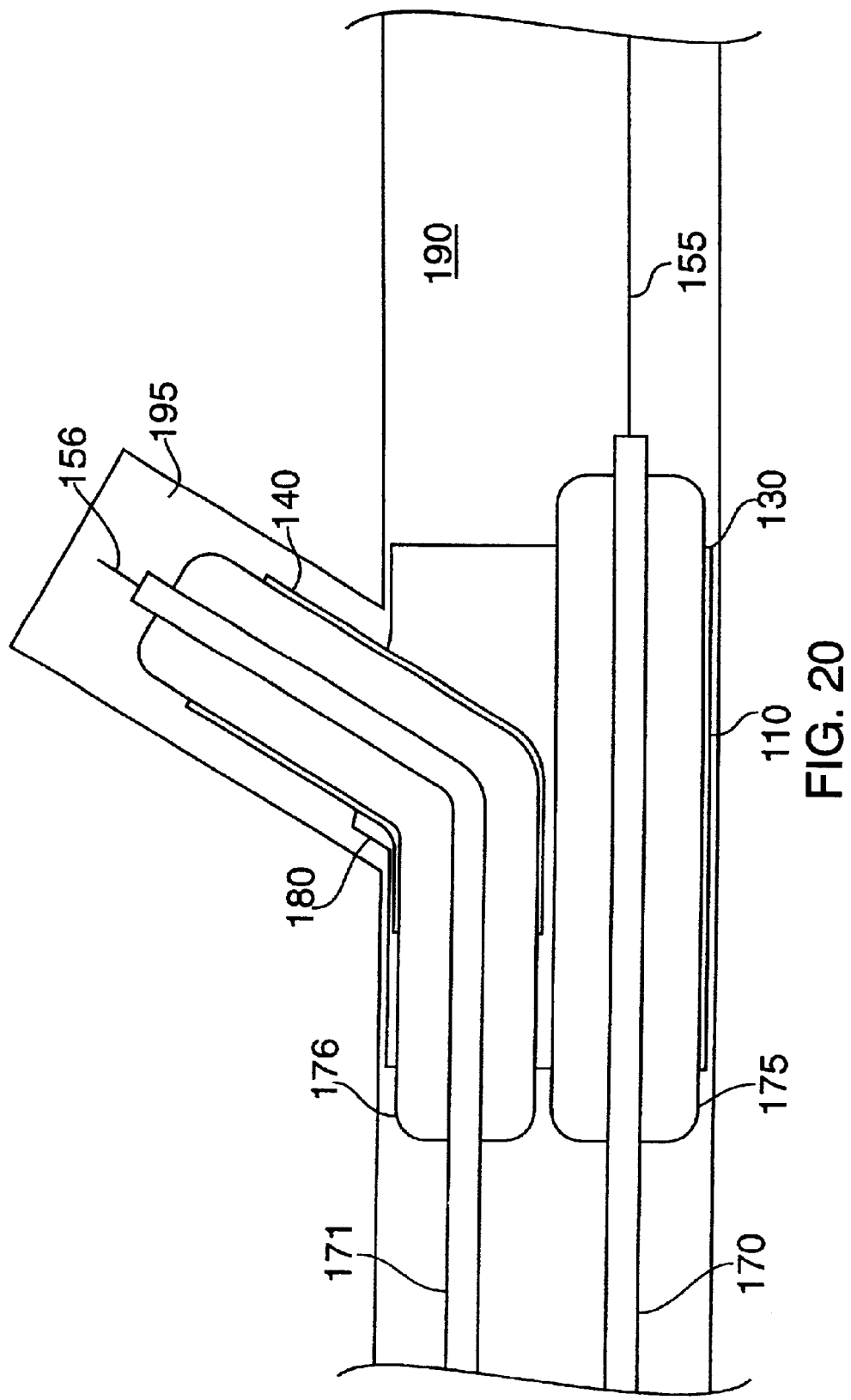
FIG. 20 shows the expansion of the second leg portion shown in FIG. 19.
Figure 21:
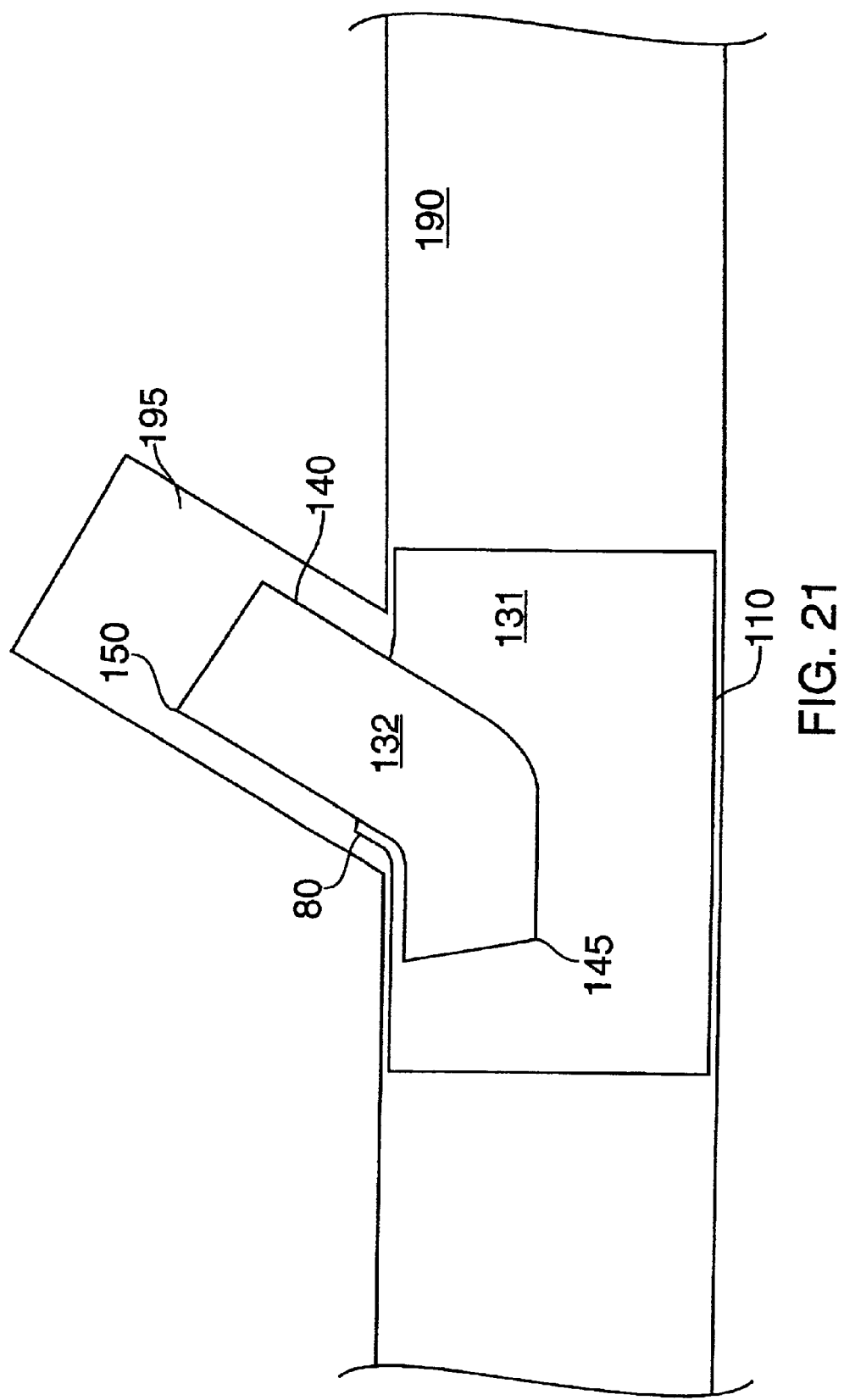
FIG. 21 shows the assembled bifurcated stent disposed in the bifurcated lumen to be treated.
Figure 24:
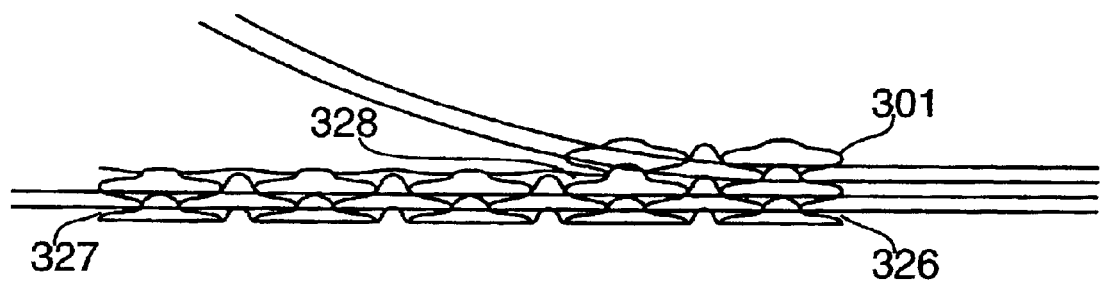
FIG. 24 shows the first expandable tubular member of FIG. 23 with catheters inserted into the longitudinal bore and the side branch aperture.
Figure 26:
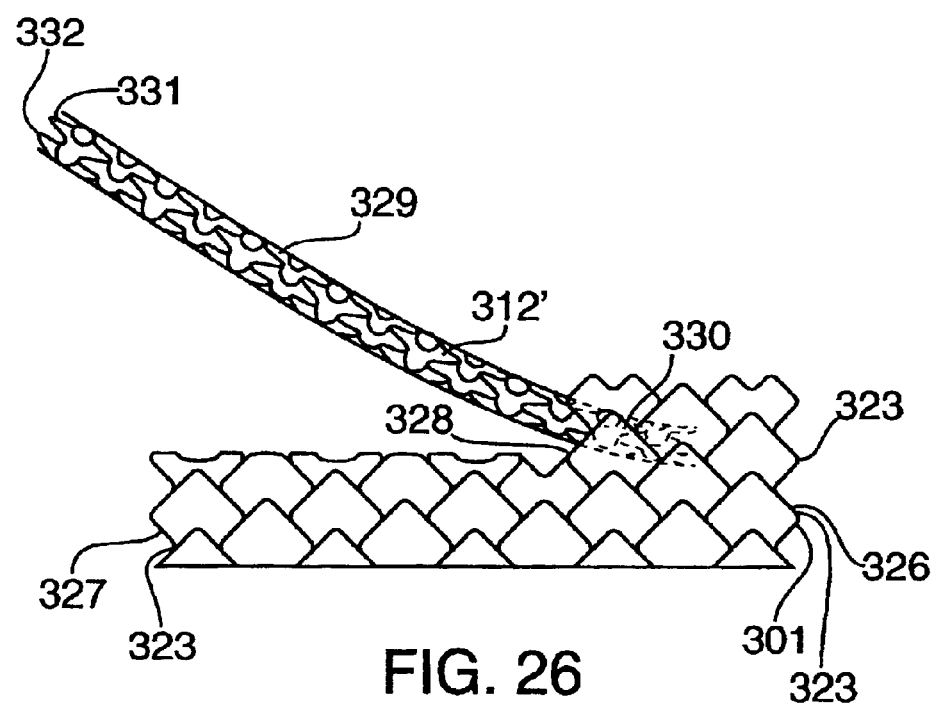
FIG. 26 shows the first expandable tubular member of FIG. 24 after expansion with an unexpanded second tubular member disposed in the side branch aperture.
Figure 25:
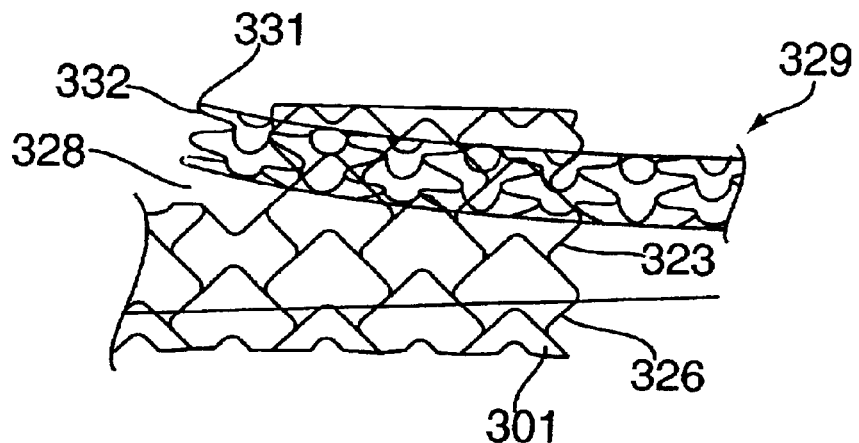
FIG. 25 shows the first expandable tubular member of FIG. 24 after expansion with an unexpanded second tubular member being introduced into the side branch aperture.
Figure 27:
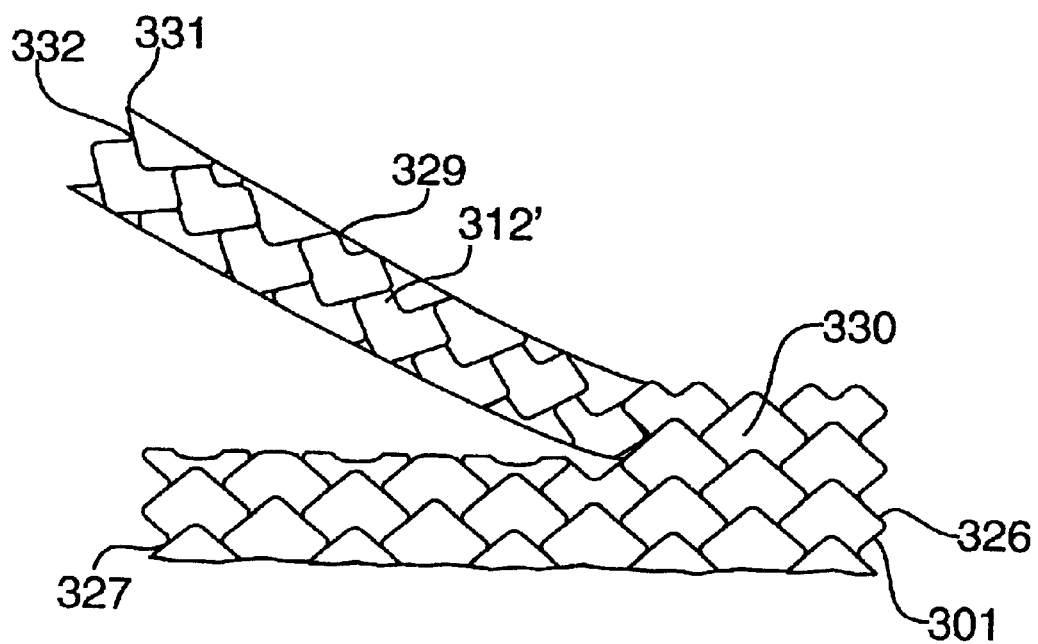
FIG. 27 shows the second tubular member of FIG. 26 after it has been expanded.
Figure 28:
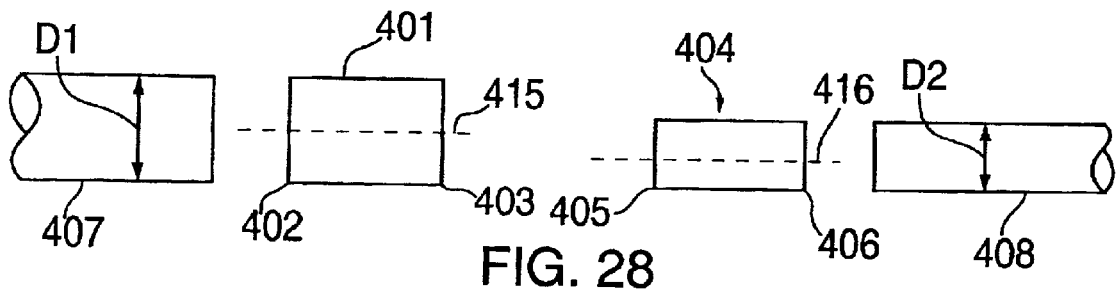
FIG. 28 shows a side view of a proximal member and a distal member used to make an alternative embodiment of the invention.
Figure 29:
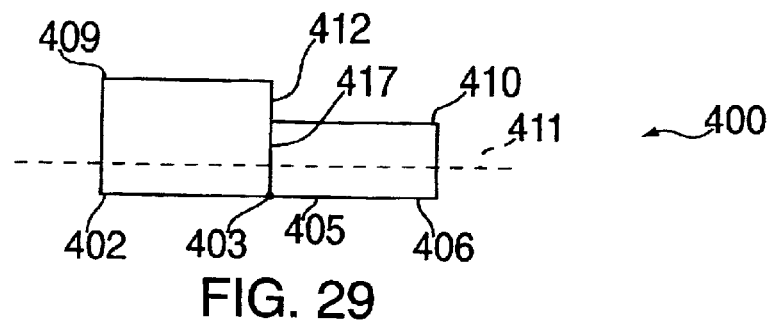
FIG. 29 shows the proximal and distal members of FIG. 28 after they have been connected to form a first expandable tubular member.
Figure 30:
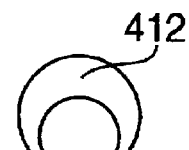
FIG. 30 is an end view of FIG. 29.
Figure 30A:
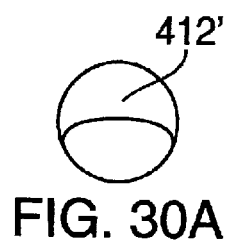
FIG. 30A is an end view of FIG. 29 showing an alternative embodiment in which a portion of the proximal member and a portion of the distal member have been deformed prior to being attached.
Figure 31:
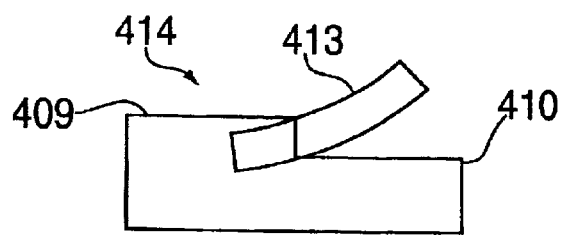
FIG. 31 shows the first expandable tubular member of FIG. 29 with a second expandable tubular member disposed within the side branch aperture.

Balloons 175 and 176 are deflated, second catheter 171 is withdrawn, and second guide wire 156 is left in place in the branch lumen 195. Second leg portion 140 is then applied to second catheter 171 so that balloon 176 is disposed in longitudinal bore 132 and second catheter 171 is then applied to second guide wire 156. Second leg portion 140 is then guided to, and introduced into, the longitudinal bore 131 of the stem and first leg portion 110 and is advanced and passed through branch aperture 135 so that the distal end 150 of the second leg portion 140 protrudes into the branch lumen 195 and the proximal end 145 communicates with longitudinal bore 131, as shown in FIG. 19. The balloon 176 on second catheter 171 is partially inflated and the balloon 175 on first catheter 170 is then partially inflated to a pressure substantially equal to the pressure in balloon 176. Both balloons 175 and 176 are then simultaneously inflated to substantially equal pressures. As shown in FIG. 20, inflation of the balloon 176 on second catheter 171 causes second leg member 140 to expand so that its external walls engage and are secured to the area surrounding aperture 135. Inflation of the balloon 175 on the first catheter 170 prevents stem and first leg portion 110 from collapsing when balloon 176 is inflated. After expansion, the external walls of second leg 140 would contact the inner wall of lumen 195, however, a gap has been intentionally left for clarity. The balloons 175 and 176 are deflated, catheters 170 and 171 and guide wires 155 and 156 are withdrawn, and the assembled bifurcated stent 160 is left in place as shown in FIG. 21.

What is claimed is:

1. A method of stenting a bifurcated vessel comprising:
   a) implanting a bifurcated stent with a balloon, said bifurcated stent having a pair of stent sections, and said balloon having a pair of inflatable sections aligned side-by-side;
   said first stent section having an opening in its lateral wall, and said second stent section capable of being placed through said lateral wall opening so that a portion of said second stent section is maintained outside said first stent section; and
   wherein said opening is sized such as to maintain said stents in close-fitting relationship to each other in a bifurcated lumen of the body
   b) guiding said stent sections on said balloon to a target area of the body;
   c) causing said second stent section to pass through the opening in said first stent section, so that at least a portion of said two stent sections are separated and a portion of said second stent section is maintained outside said first stent section;
   d) inflating said inflatable sections, to thereby expand said stent sections, and said second stent section expanded sufficiently to maintain said stents in close-fitting relationship to each other in said target area.

2. The method of claim 1 wherein said stent further comprises:
   the first stent section having first and second ends with an intermediate section therebetween, the first stent further having a longitudinal axis and, wherein said intermediate section has the opening therein; and
   the second stent section having first and second ends with an intermediate section therebetween, the second stent further having a longitudinal axis; and
   each of said stent sections expandable from a first diameter to a larger second diameter; and
   wherein said second stent section is configured in its said first diameter passing through a cell of the first stent section.

3. The method of claim 2, wherein each said stent sections is patterned or etched with perforations forming a pattern that allows the first and second stent sections to expand from a first configuration to an expanded configuration.

* * * * *